(12) United States Patent
Cho et al.

(10) Patent No.: US 10,443,027 B2
(45) Date of Patent: Oct. 15, 2019

(54) APPARATUS FOR CLEARING TISSUE USING ELECTROPHORESIS

(71) Applicant: LOGOS BIOSYSTEMS, INC., Anyang, Gyeonggi-Do (KR)

(72) Inventors: Keun Chang Cho, Seoul (KR); Neon Cheol Jung, Gyeonggi-do (KR)

(73) Assignee: LOGOS BIOSYSTEMS, INC., Anyang, Gyeonggi-do (KR)

( * ) Notice: Subject to any disclaimer, the term of this patent is extended or adjusted under 35 U.S.C. 154(b) by 0 days.

(21) Appl. No.: 15/401,619

(22) Filed: Jan. 9, 2017

(65) Prior Publication Data

US 2017/0114313 A1    Apr. 27, 2017

Related U.S. Application Data

(63) Continuation of application No. PCT/KR2015/006717, filed on Jun. 30, 2015.

(30) Foreign Application Priority Data

Jul. 7, 2014 (KR) .................. 10-2014-0084705

(51) Int. Cl.
  *G01N 27/453* (2006.01)
  *C12M 1/42* (2006.01)
  (Continued)

(52) U.S. Cl.
  CPC .............. *C12M 35/02* (2013.01); *C12M 1/00* (2013.01); *C12M 1/42* (2013.01); *C12M 3/00* (2013.01);
  (Continued)

(58) Field of Classification Search
  CPC ......... C12M 3/00; C12M 3/06; G01N 27/447; G01N 27/44704; G01N 27/44708; G01N 27/44752; G01N 27/453
  See application file for complete search history.

(56) References Cited

U.S. PATENT DOCUMENTS 4,541,910 A * 9/1985 Davis, III .......... G01N 27/4473
  204/456
4,909,920 A * 3/1990 Sarrine ............ G01N 27/44721
  204/457

(Continued)

FOREIGN PATENT DOCUMENTS

JP    H11337522 A    12/1999
WO    2004/078253 A2    9/2004
(Continued)

OTHER PUBLICATIONS

Bio-Rad Criterion™ Blotter Instruction Manual—Catalog Nos. 170-4070 and 170-4071, downloaded Jan. 15. 2019 (Year: 2019).*
(Continued)

*Primary Examiner* — Alexander S Noguerola
(74) *Attorney, Agent, or Firm* — Mintz Levin Cohn Ferris Glovsky and Popeo, P.C.; Kongsik Kim; Carolina Säve

(57) ABSTRACT

An apparatus for clearing tissue using electrophoresis according to an embodiment of the present invention comprises: a chamber which can contain therein a buffer solution and the biological tissue and has an inlet port and an outlet port for circulating the buffer solution; a support member, located within the chamber, for supporting the biological tissue; and electrodes located within the chamber and formed separately of a first electrode and a second electrode which correspond to each other. With the apparatus, it is possible to minimize the degradation of decomposition efficiency and quickly clear the tissue compared to a conventional apparatus.

13 Claims, 12 Drawing Sheets

(51) Int. Cl.
*C12M 3/00* (2006.01)
*C12M 1/00* (2006.01)
*C12M 1/12* (2006.01)
*G01N 27/447* (2006.01)

(52) U.S. Cl.
CPC ....... *C12M 25/06* (2013.01); *G01N 27/44704* (2013.01); *G01N 27/453* (2013.01)

(56) References Cited

U.S. PATENT DOCUMENTS

| | | | | |
|---|---|---|---|---|
| 4,959,133 | A | * | 9/1990 | Adcock ............ G01N 27/44739 204/457 |
| 5,047,136 | A | * | 9/1991 | Beritashvili ............ B01D 57/02 204/609 |
| 5,165,898 | A | * | 11/1992 | Chu ................. G01N 27/44704 204/607 |
| 7,556,726 | B2 | * | 7/2009 | Herrera Isidron .......................... G01N 27/44713 204/609 |
| 2003/0089607 | A1 | * | 5/2003 | Rivern Rojas ... G01N 27/44704 204/458 |
| 2011/0076665 | A1 | | 3/2011 | Gatenholm et al. |

FOREIGN PATENT DOCUMENTS

| | | | |
|---|---|---|---|
| WO | 2013/098887 A1 | 7/2013 | |
| WO | WO 2014025392 A1 * | 2/2014 | ............... G01N 1/28 |

OTHER PUBLICATIONS

2002 Bio-Rad Sales Product List, downloaded Jan. 15. 2019 (Year: 2002).*

Chung, Kwanghun et al., "Structural and molecular interrogation of intact biological systems", Nature, vol. 497, May 16, 2013, pp. 332-339.

* cited by examiner

APPARATUS FOR CLEARING TISSUE USING ELECTROPHORESIS

CROSS-REFERENCE TO RELATED APPLICATIONS

The present application is a continuation application of International Application No. PCT/KR2015/006717 filed on Jun. 30, 2015, which claims priority to Korean Application No. 10-2014-0084705 filed on Jul. 7, 2014, which applications are incorporated herein by reference.

TECHNICAL FIELD

The present invention claims priority to the KR patent application no. 10-2014-0084705 filed on Jul. 7, 2014, and the entire contents of which are incorporated by reference in their entireties. The present invention relates to an apparatus for clearing tissue using electrophoresis. More specifically, the present invention relates to an apparatus for removing tissue constituents or components by using electrophoresis.

BACKGROUND ART

The CLARITY, a method of tissue clearing, was developed by Karl Deisseroth et al. at the Stanford University of the US in 2013, and published in "Nature" (Chung K et al., Nature, 497: 332-337 (2013)).

Specifically, according to this method, certain components within a biological tissue are replaced with an exogenous material of hydrogel, which results in transparent tissue and accordingly allows it to be optically detected. That is, this method is to visualize brain tissue by separating lipid components in the brain through a chemical treatment process.

In accordance with the conventional anatomical methods for analyzing microscopic structure and neuronal networks in a brain, the brain tissue is cut into thin slices to understand the respective neuronal networks thereof first, and followed by the integration of the large amount of information obtained from the slices to analyze overall structure of the brain cells and molecular distribution.

The CLARITY method of Karl Deisseroth et al., however, is worthwhile in that it makes it possible to detect neuronal networks using a transparent brain tissue in macroscopic or molecular level without impairing the tissue, unlike the conventional methods. Therefore, the CLARITY is expected to highly contribute in the brain disease research and biological tissue assays, etc.

FIG. 1, which is included in the Nature above, illustrates the CLARITY method and briefly explains a device for clearing lipid components from mouse brain tissue. In accordance with the FIG. 1, the brain of a mouse is contained in a chamber at first, and platinum wires are placed on opposite sides of the tissue, and then 10~60 V electricity is applied thereto to separate the lipid components from the tissue by electrophoresis. While the negative charges (anions) (−) generated from the cathode move to the anode during the electrophoresis, ionized micelles surrounding the lipid components separate the lipid from the brain and keep on moving to the anode. Meanwhile, the chamber has a pair of inlet port and outlet for circulating the buffer solution which is circulated by a water circulator. Such a circulation is carried out for the secure of buffering capacity and replacing contaminated buffer solution. In addition, the circulation of buffer solution is used to reduce temperature in the chamber when the temperature therein is elevated by the electricity application.

However, the CLARITY method has a few drawbacks as follows: i) The surface area of the electrodes is small but the resistance is high compared to the plate electrodes since it employs wire electrodes, and thereby relatively higher electric voltage is applied to the electrodes at the same electric current. Further, the higher voltage results in high temperature heat generation, which increases the amount of side reactions, such as, electrolysis of water or organic materials, and accelerates contamination rate of the solution. ii) It is difficult to control heat generation since it is not easy to cool down the wire electrodes comparing to the plate electrodes. iii) The buffer solution circulates as rapidly as several litters per minute, so that it increases the amount of the side reactions. iv) It takes from 5 days to 9 days to separate lipid components from mouse brain using the CLARITY method.

In this regard, it is still required to develop a novel tissue clearing method which can remove or separate lipid components or constituents form a biological tissue more rapidly, while controlling heat generation and decreasing circulation rate of buffer solution to reduce the amount of side reactions.

SUMMARY

We inventors have been researched a lot to develop a tissue clearing apparatus which can remove lipid components from a biological tissue in more stable, efficient and rapid way. As a result, we inventors completed this invention by finding out that plate electrodes rather than wire electrodes provide more stable and rapid lipid clearing from the brain tissue.

The purpose of the present invention is to provide a tissue clearing apparatus using electrophoresis for clearing components or constituents from a biological tissue, wherein the apparatus employs plate type electrodes.

Another purpose and advantages of the present invention will be clearly understood by the following detailed descriptions of the invention, claims and drawings.

In accordance with an exemplary embodiment of the present invention, a tissue clearing apparatus using electrophoresis for clearing components from a biological tissue is provided, wherein the apparatus is characterized by the followings.

(a) a chamber able to contain buffer solution and a biological tissue, wherein the chamber has an inlet port and an outlet port therein for the circulation of the buffer solution; and (b) a first electrode and a second electrode separately placed in two opposite positions in the chamber, wherein each electrode is shaped in flat plate.

Further, each area of the first electrode and the second electrode may be not less than 1 mm, and the distance between the first electrode and the second electrode may be not less than 10 mm.

Further, a fixed electric current may be applied through the first electrode and the second electrode. Specifically, the fixed electric current may be between 0.5 to 3 A (ampere).

The tissue clearing apparatus using electrophoresis of the present invention may further comprise a control part to switch polarities of the first electrode and the second electrode to each other. In addition, a support member for supporting the biological tissue may be further comprised in the chamber. The support member may be rotatable.

Further, according to another exemplary embodiment of the present invention, each of the first electrode and the second electrode may have two or more electrodes to correspond to each other, and the first electrode and the second electrode may be placed in two opposite positions, and a control part may be additionally installed to control any one of two or more first electrodes and any one of two or more second electrodes to operate mutually. In this case, the control part may be configured to switch the polarities of the first electrode and the second electrode to each other.

Further, according to yet another exemplary embodiment of the present invention, the first electrode may consist of one electrode and the second electrode may consist of two electrodes, and the first electrode and the second electrodes may be placed in opposite two positions to correspond to each other, and a control part may be further configured to control the first electrode and any one of the second electrodes so that they operate mutually.

In addition, the tissue clearing apparatus using electrophoresis of the present invention may further comprise the followings.

(a) a cooling plate connected to the outside of the chamber; and (b) a thermoelement for cooling down the cooling plate.

The cooling plate may consist of at least one cooling plate and is connected to each of the external regions of the first electrode and the second electrode. The thermoelement may consist of at least one thermoelement, which is connected to the external region of the cooling plate, and may further comprise at least one heat sink which is connected to the external region of the thermoelement and has a number of cooling pins. In addition, at least one cooling fan, which is placed the outside of the heat sink and circulates the surface air thereon, may be further installed.

The features and advantages of the present invention are summarized as below:

(a) The present invention provides a tissue clearing apparatus using electrophoresis to separate components or constituents of a biological tissue.

(b) The present invention employs plate electrodes and is characterized in that the polarity of the electrodes can be switched to each other.

(c) The apparatus of the present invention can suppress rapid temperature increase to reduce the circulation rate of the buffer solution circulating through the inlet port and the outlet port. Therefore, the present invention can reduce the amount of side reactions and minimize the clearing efficiency decrease, and accordingly rapid lipid clearing can be achieved, in comparison to the conventional devices.

DETAILED DESCRIPTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Figure 2:
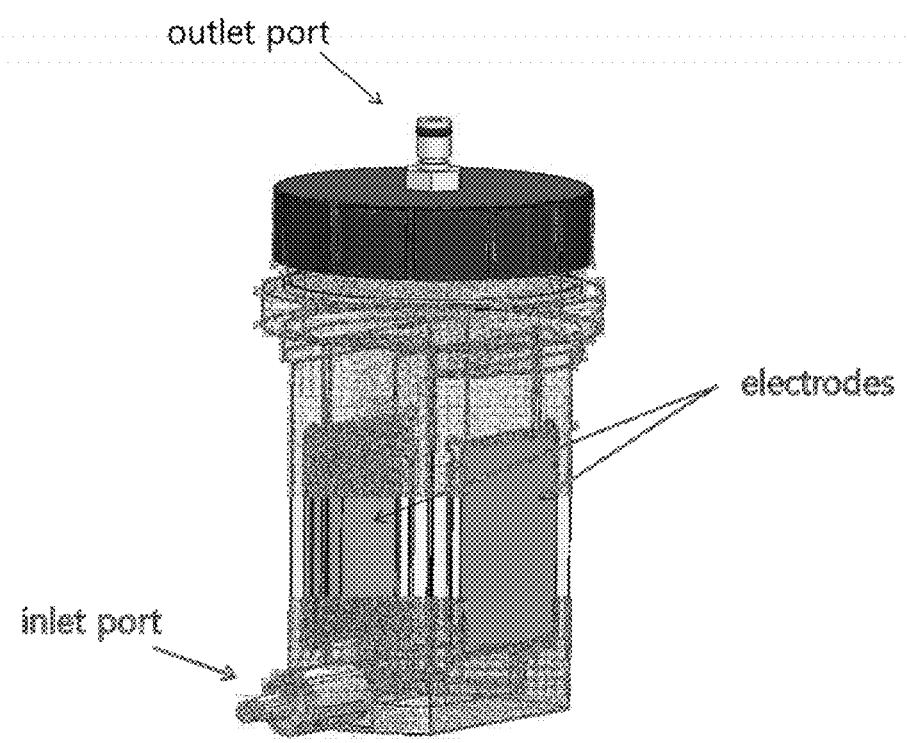
FIG. 2 is a perspective view of a tissue clearing apparatus of the present invention according to an exemplary embodiment.
Figure 3:
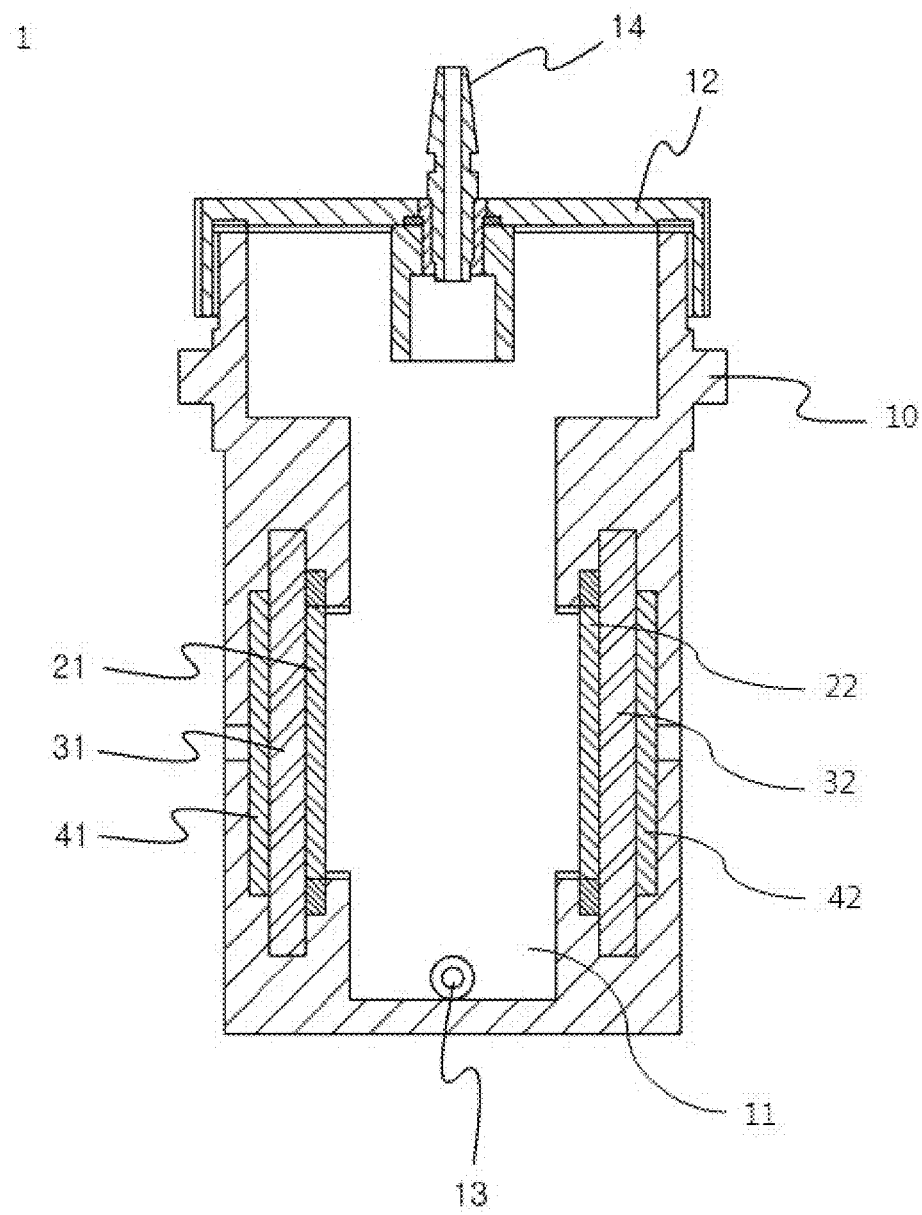
FIG. 3 is a section view of the tissue clearing apparatus of the FIG. 2.

The FIG. 2 is a perspective view of the tissue clearing apparatus using electrophoresis of the present invention (1), the FIG. 3 is a section view of the tissue clearing apparatus (1) of the FIG. 2.

The tissue clearing apparatus using electrophoresis of the present invention (1) is used for separating or removing certain components or constituents of a biological tissue. Experiments for clearing lipid components from a mouse brain was performed to assess the efficiency of the present invention. Hereinafter, the present invention is explained with reference to the results of experiments.

Figure 1:
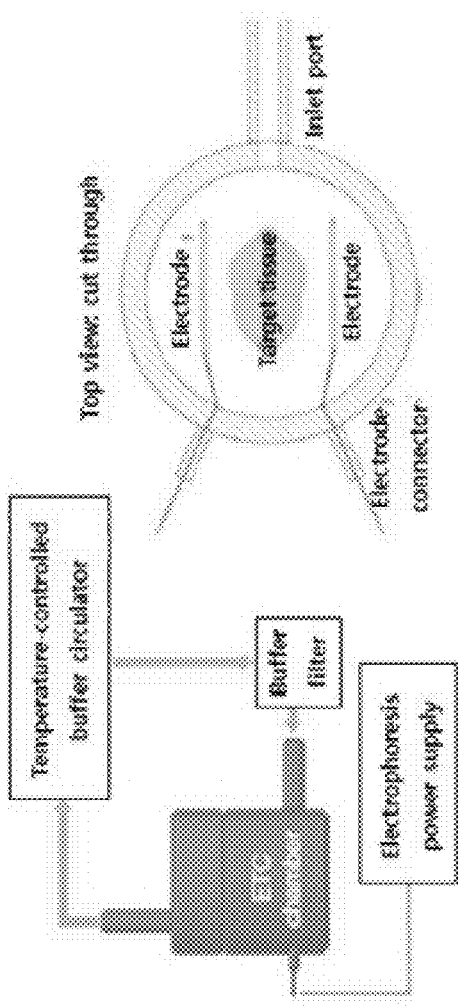
FIG. 1 is a schematic drawing of a conventional brain lipid clearing device using electrophoresis.

The tissue clearing apparatus using electrophoresis of the present invention (1) comprises a chamber (10) and electrodes (21, 22) as shown in the FIG. 1 or FIG. 3.

The present invention relates to an apparatus for clearing certain components from a biological tissue using electrophoresis, and in particular, relates to an apparatus for rapidly clearing lipid on the surface of brain without giving damage thereto.

A buffer solution of electrolyte for electrophoresis is filled into the inside (11) of the chamber (10), and a brain, the target for clearing, is contained in the chamber as well.

For this purpose, the chamber has a container shape, and the upper part of the chamber may have a cover (12) which is separably connected to the chamber (10). In addition, an inlet port (13) and an outlet port (14) for the inflow and outflow of the buffer solution may be equipped in the chamber (10), and thereby the buffer solution circulates through the inlet port (13) and outlet port (14).

A first electrode and a second electrode are separately placed in two opposite positions in the chamber, and each electrode is plate electrode (plat-shaped, for example, tablet or curved-shape plate). A pair of the first electrode (21) and the second electrode (22) are positioned to correspond to each other on the opposite two sides, and may be placed to form different inner walls of the chamber. That is, one of the first electrode (21) and the second electrode (22) is placed on a side inner wall, and the other is placed on the opposite side inner wall of the chamber (10).

Further, it is preferable for the first electrode (21) and the second electrode (22) to have larger surface area than the projected area of the biological tissue, such as brain tissue. Accordingly, the electric field generated by the first electrode and the second electrode influences over entire biological tissue to be treated, and thereby rapid clearing is performed during the electrophoresis. Specifically, each area of the first electrode and the second electrode is not less than 1 cm$^2$ and the distance between two electrodes is not less than 10 mm.

When electricity is applied to the first electrode (21) and the second electrode (22), negatively charged ions (anions) (−) generated from the cathode surround and separate lipid components from the brain while they keep moving toward the anode.

The tissue clearing apparatus using electrophoresis of the present invention (1), which employs plate electrodes rather than wire electrodes, can apply higher electric current with relatively lower voltage, since the plate electrodes give rise to low heat generation rate and a small amount of side reactions compared to the wire electrodes. For example, 0.5~3 A electric current can be applied with 10~60 V voltage.

In this regard, since the electrophoresis tissue clearing apparatus of the present invention has low heat generation rate comparing to the conventional device having wire electrodes, there is no need to increase buffer solution circulation rate for reducing temperature in the chamber and it is possible to minimize clearing efficiency reduction by the decreased amount of side reactions. Therefore, the apparatus of the present provides a way to remove or separate lipid components more quickly than the conventional device.

Figure 5:
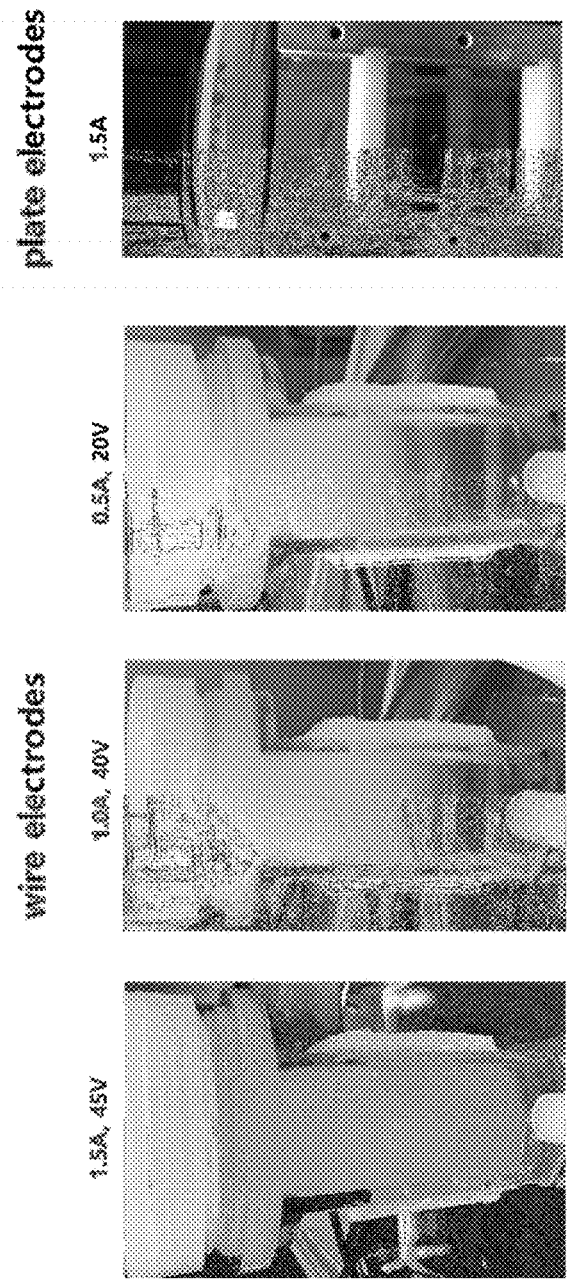
FIG. 5 is a photograph showing the comparison results of water electrolysis by using the conventional wire type electrodes and plate type electrodes of the present invention.
Figure 6:
FIG. 6 is a photograph showing the comparison results of color change of buffer by using the conventional wire type electrodes and plate type electrodes of the present invention.

FIG. 5 shows the photograph which compares the water electrolysis results by using the conventional wire electrodes and the electrodes of the present invention, respectively. It explains that water electrolysis was stably performed with higher electric current when the plate electrodes were used, in comparison to the wire electrodes. FIG. 6 shows the photographs of the experimental results of the respective use of the conventional wire electrodes and the plate electrodes of the present invention in the buffer for separating lipid components. In accordance with the FIG. 6, the side reactions did not increase by using the plate electrodes of the present invention even for 24 hours treatment. Therefore, the color change level of the buffer was significantly lower than the conventional wire electrodes.

Figure 7:
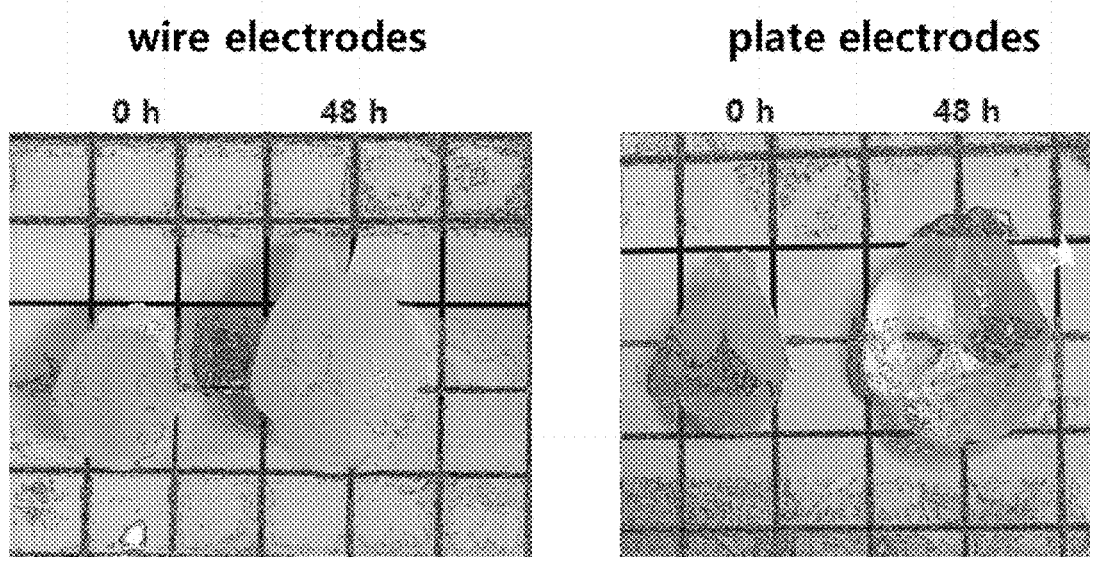
FIG. 7 is a photograph showing the comparison results of lipid removal the brain tissue detected 48 hours after the treatment by using the conventional wire type electrodes and plate type electrodes of the present invention.

FIG. 7 shows the results of mouse brain tissue clearing results by using the conventional wire electrodes and the plate electrodes of the present invention respectively, for 48 hours. The lipid components in the mouse brain were efficiently cleared by using the plate electrodes rather than wire electrodes.

Figure 4:
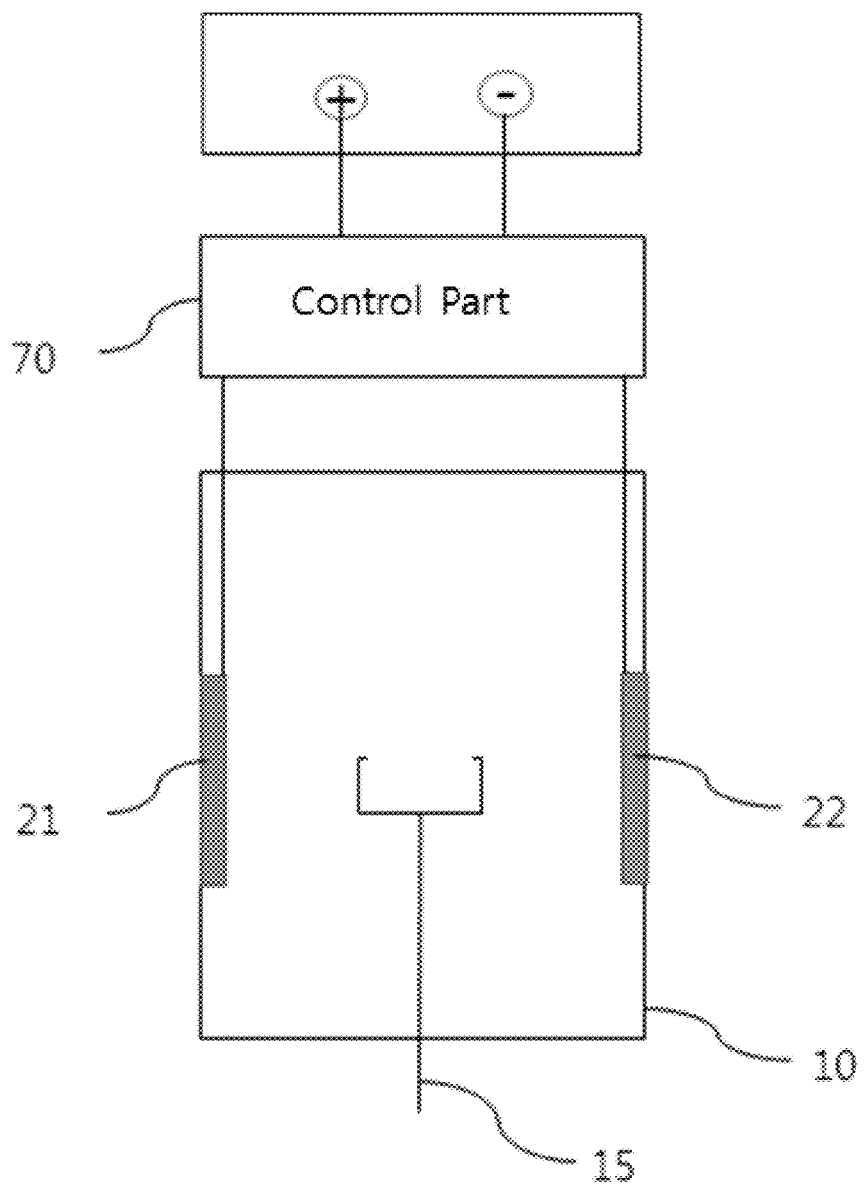
FIG. 4 is a schematic view of a tissue clearing apparatus of the present invention according to another exemplary embodiment.

According to the tissue clearing apparatus using electrophoresis of the present invention (1), electricity may be applied to the first electrode (21) and the second electrode (22) in a fixed direction, but the polarities of the first electrode (21) and the second electrode (22) may be switched to each other. For this purpose, a control part (70) as shown in FIG. 4 may be additionally installed, and the control part (70) changes the direction of the electric current supplied by the electric power supplier to switch the polarities of the first electrode (21) and the second electrode (22). The control part (70), which is a means for switching polarities, may be a mechanical switching device type or a semiconductor device, such as, IC and transistor, etc.

The polarity switching by the control part (70) may be performed over a fixed time interval or changed time intervals, for example, 10 minutes, 1 minute and 10 seconds. The direction of the anions (−) movement generated from the first electrode or the second electrode is changed by the polarity switching, and thereby the removal or separation of the lipid components is performed in various regions of the brain. Therefore, the lipid components can be cleared rapidly.

Figure 8:
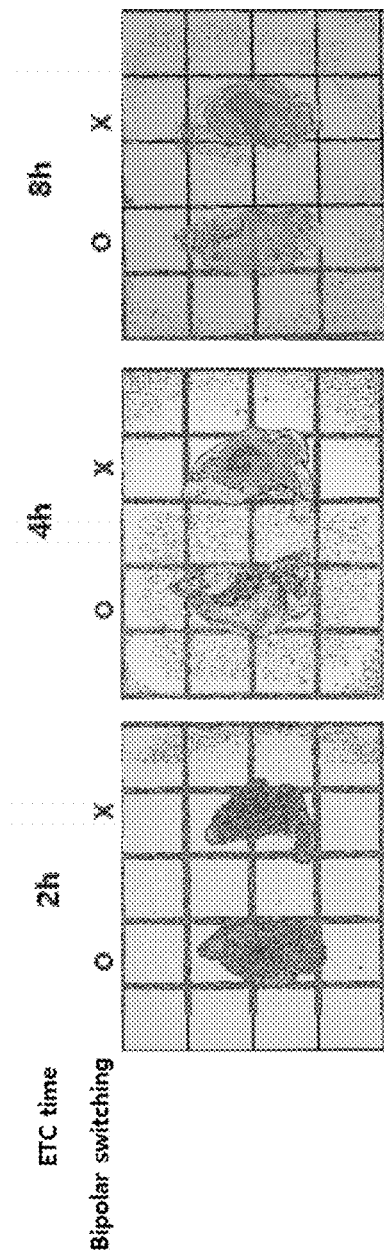
FIG. 8 is a photograph showing the comparison results of lipid removal by using the tissue clearing apparatus of the present invention with or without polarity switching.

FIG. 8 is the photograph showing the results of lipid clearing experiments performed by repetitively switching the polarities of the first electrode (21) and the second electrode (22) to each other in the electrophoresis tissue clearing apparatus (1), with a fixed time interval of 1 minute. FIG. 8 shows and compares the photos of the experimental results obtained by the treatments for 2 hours, 4 hours and 8 hours respectively, with no polarity switch and with polarity switch. When the polarity was switched, the lipid components were cleared more efficiently from the mouse brain to make the brain tissue transparent.

In accordance with these results, it is confirmed that if the polarities of the first electrode (21) and the second electrode (22) are switched to each other, in particular, with a short time interval, the lipid components are efficiently cleared from the tissue.

Further, a support member (15) may be additionally included in the tissue clearing apparatus using electrophoresis of the present invention (1) (FIG. 4). The support member (15) is configured to support the biological tissue (brain) in the chamber (10), and may be made to rotate. If the support member (15) rotate, the directions of anion movement with respect to the brain are changed. That is, the direction of electric field formation between the first electrode (21) and the second electrode (22) is changed, and thereby rapid clearing of the lipid components is achieved.

According to the tissue clearing apparatus using electrophoresis of the present invention (1), each of the first electrode (21) and the second electrode (22) may consist of one electrode or two or more electrodes as shown in FIG. 7. When two or more first electrodes (21) and two or more second electrodes (22) are included, they may be placed in circumferential directions with respect to the center of the chamber (10). That is, a number of the first electrodes (21a, 21b, 21c) may be placed in circumferential directions with respect to the center of the chamber (10), and a number of the second electrodes (22a, 22b, 22c) may be placed in circumferential directions with respect to the center of the chamber (10) as well. In this case, the number of the second electrodes (22a, 22b, 22c) may be the same as that of the first electrodes (21a, 21b, 21c). Preferably, a number of the first electrodes and a number of the second electrodes are positioned to have the same distance between neighboring electrodes.

Figure 9:
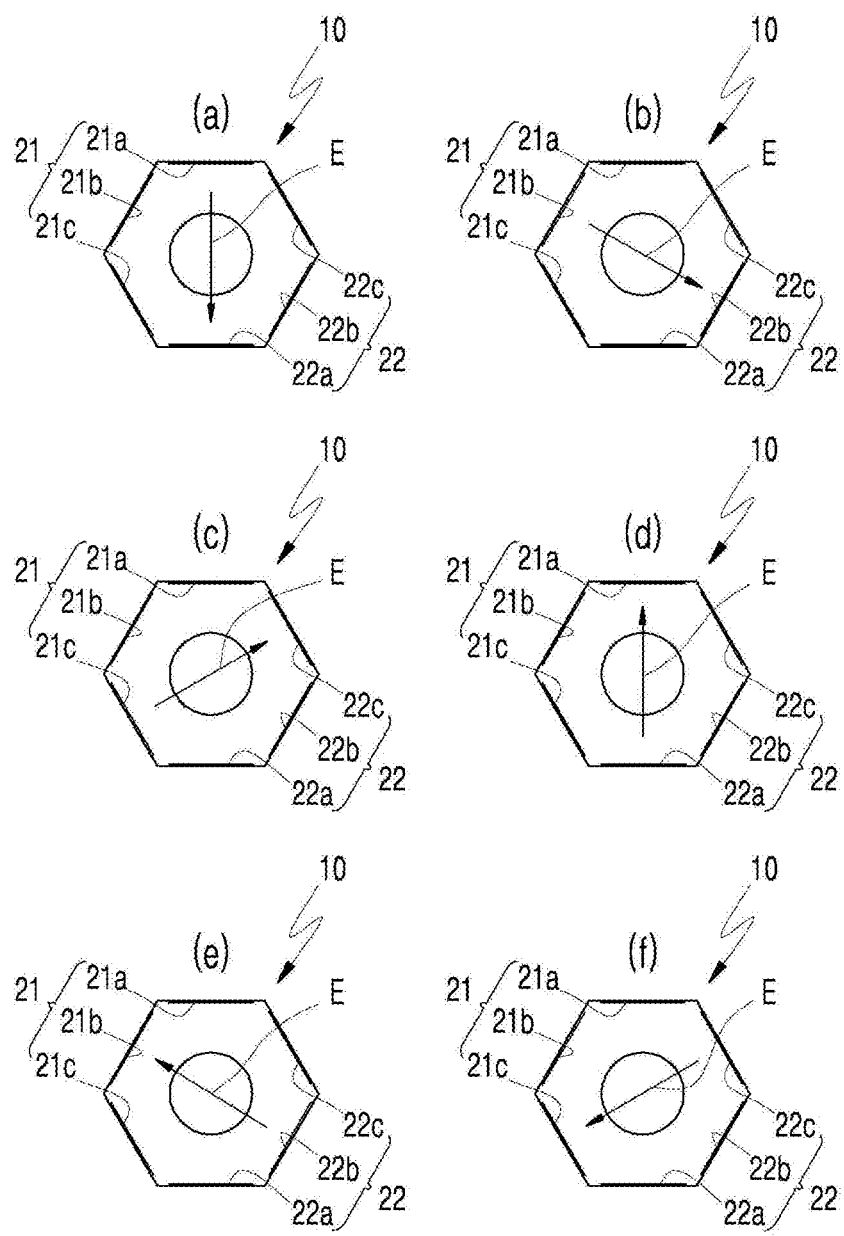
FIG. 9 and FIG. 10 are schematic views of electrode operations in the tissue clearing apparatus using electrophoresis of the present invention.

In this case, the control part (70) can control any one of the two or more first electrodes (21a, 21b, 21c) and any one of the two or more second electrodes (22a, 22b, 22c) so that they operate mutually. That is, the control part (70) may control the first electrode (21a) and the second electrode (22b) to operate mutually while the other first electrodes (21b, 21c) and second electrodes (22b, 22c) do not operate; or may control the first electrode (21b) and the second electrode (22b) to operate mutually while the other first electrodes (21a, 21c) and second electrodes (22a, 22c) do not operate. Further, the control part (70) may be configured to change the operating first electrode (21a, 21b, 21c) and second electrode (22a, 22b, 22c) in accordance with the circumferential direction. That is, the control part (70) may control the direction of electric field (E) generated by the first electrodes (21a, 21b, 21c) and the second electrodes (22a, 22b, 22c) so as to continuously change along the clockwise or counterclockwise direction (FIG. 9(a) to FIG. 9(c)).

Further, the control part (70) may control the polarities of the first electrodes (21a, 21b, 21c) and the second electrodes (22a, 22b, 22c) so that they are switched to each other, and accordingly the direction of the electric field generated by the first electrodes (21a, 21b, 21c) and the second electrodes (22a, 22b, 22c) may continuously change in clockwise or counterclockwise direction and circulates repeatedly as well (FIG. 9(a) to FIG. 9(f)).

According to such a configuration of the first electrode (21) and the second electrode (22) and the control by the control part (70), the direction of anion movement with respect to the brain varies sequentially, and thereby lipid clearing can be performed quickly.

Figure 10:
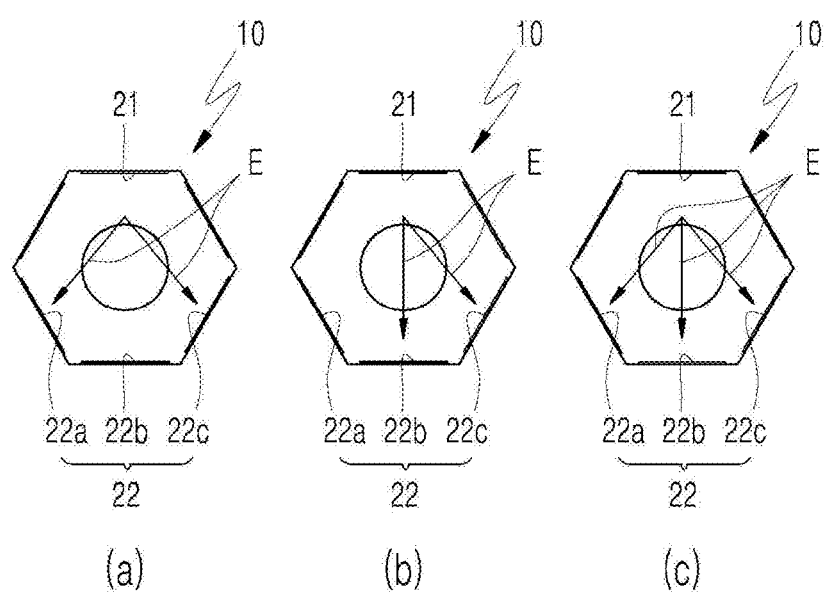

FIG. 10 is a schematic view illustrating the operation mode of the electrodes of the tissue clearing apparatus using electrophoresis according to yet another exemplary experiment of the present invention. In accordance with the tissue clearing apparatus (1), the first electrode (21) and the second electrode (22) are placed in circumferential directions with respect to the chamber (10) center, wherein the first electrode (21) or the second electrode (22) consists of two or more electrodes. That is, a number of the first electrodes (21) or the second electrodes (22) may be placed in circumferential directions with respect to the chamber (10) center. FIG. 10 illustrates an exemplary embodiment, wherein the first electrode (21) consists of one electrode and the second electrodes (22a, 22b, 22c) consist of a number of electrodes. It is preferable that the first electrode (21) and the second electrodes (22a, 22b, 22c) are placed to have the same distance between neighboring electrodes. Further, the control part (70) may control the first electrode (21) and the second electrodes (22a, 22b, 22c) to operate mutually in various patterns. For example, as shown in FIG. 10, when the second electrode consists of a number of electrodes (22a, 22b, 22c), the control part (70) may sequentially switch the second electrodes (22a, 22b, 22c), which operate mutually with the first electrode (21), from one to another. That is, it may be controlled that one of the second electrodes (22a) operates first, another second electrode (22b) operates, and then the other second electrode (22c) operates. Therefore, the direction of the generated electric field (E) may be controlled to change. Otherwise, the control part (70) may be configured to control the operating second electrodes (22a, 22b, 22c) to be switched from one to another while two or more second electrodes (22a, 22b, 22c) keep operating mutually with the first electrode (21) at the same time. As illustrated in FIG. 10(a) and FIG. 10(b), it may be controlled that a pair of second electrodes (22a, 22c) operate and thereafter another pair of second electrodes (22b, 22c) operate. Otherwise, the control part (70) may be configured to vary the number of the second electrodes (22a, 22b, 22c) mutually operating with the first electrode (21). As shown in FIG. 10(b) and FIG. 10(c), it may be controlled that two second electrodes (22b, 22c) operate and then three second electrodes (22a, 22b, 22c) operate. In this regard, the direction of anions movement with respect to the brain is changed in numerous patterns by the various combinations of operating mode of the first electrode (21) and the second electrode (22) and the control part (70), and accordingly lipid components are cleared rapidly.

In addition, the tissue clearing apparatus using electrophoresis of the present invention (1) may additionally comprise a cooling plate (31, 32) and a thermoelement (41, 42).

The cooling plate (31, 32) and the thermoelement (41, 42) are used for reducing temperature inside of the chamber. The cooling plate (31, 32), which is connected to the outside of the chamber (10), has flat-plate shape (for example, tablet or curved plate shape) and consists of a metal having relatively excellent thermal conductivity. For example, gold, silver, copper, aluminum or alloy thereof may be used. Specifically, the cooling plate (31, 32) may be configured to closely adhere and directly connected to each of the first electrode and the second electrode outside of the chamber (10). In addition, the cooling plate (31, 32) may be installed symmetrically in two opposite sides like the electrodes.

The thermoelement (41, 42) may be shaped as a common thermoelement (41, 42) absorbing heat by Peltier effect to cool down ambient temperature, and the thermoelement (41, 42) is closely connected to the external region of the cooling plate (31, 32). A pair of the thermoelements (41, 42) are placed symmetrically in the external region of the cooling plate (31, 32), and electric power suppliers are provided for each of the thermoelements (41, 42). Further, a temperature sensor may be connected to the thermoelement for the accurate control of temperature.

Figure 11:
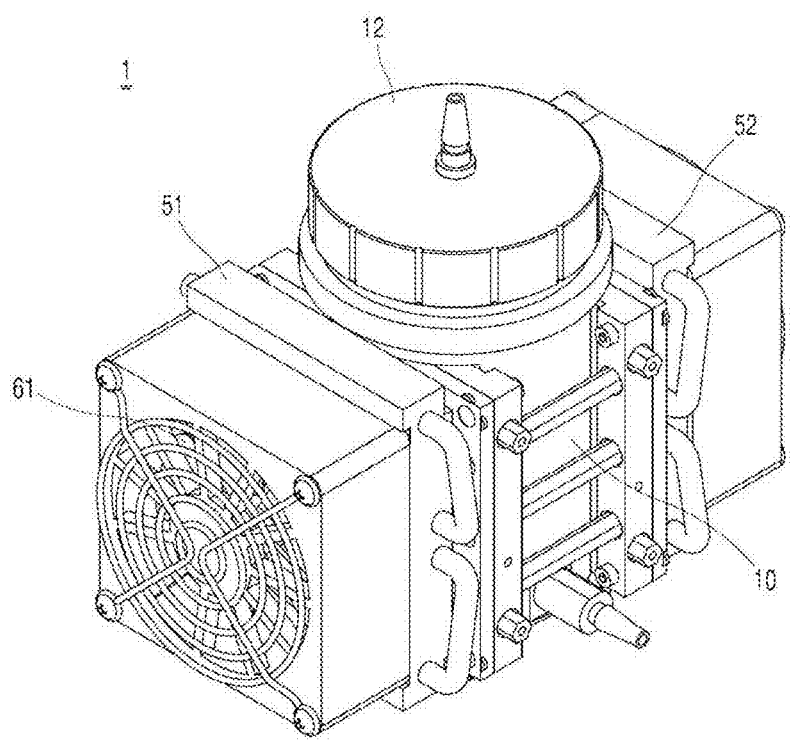
FIG. 11 is a perspective view of the tissue clearing apparatus using electrophoresis of the present invention according to yet another exemplary embodiment.
Figure 12:
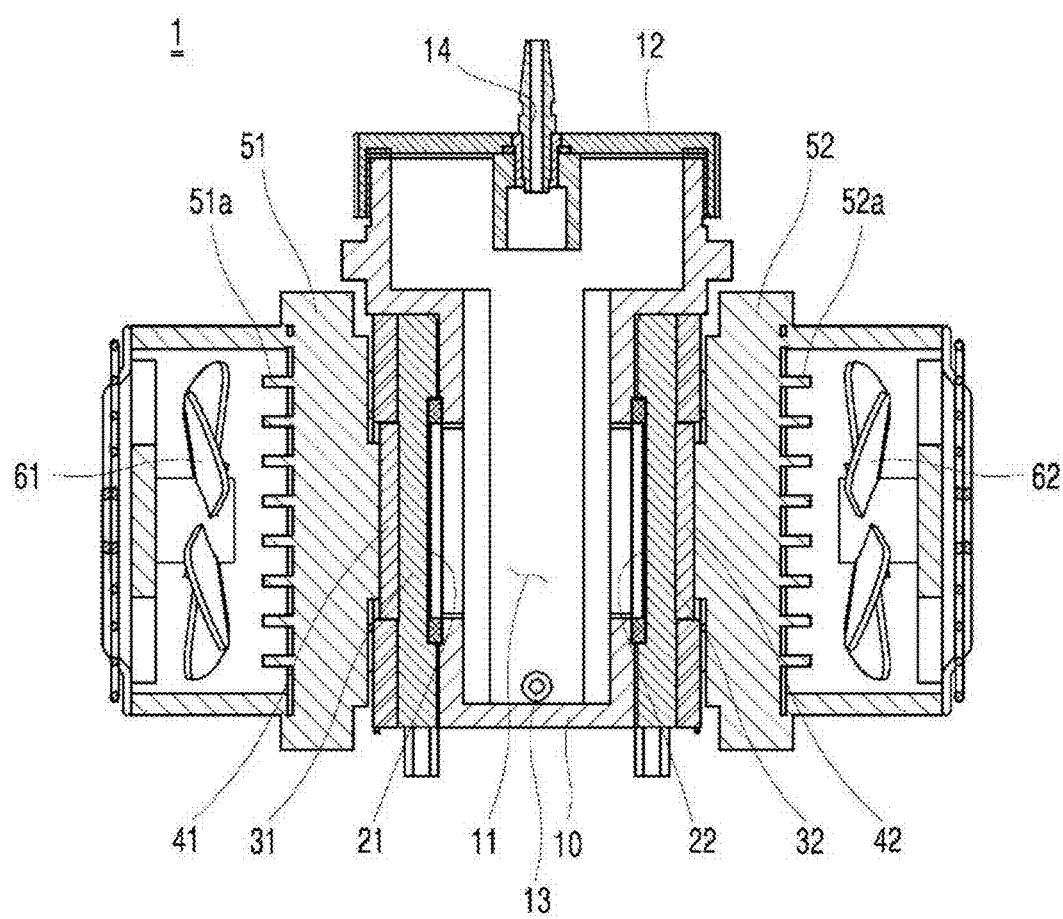
FIG. 12 is a section view of the tissue clearing apparatus of the FIG. 11.

Further, the tissue clearing apparatus using electrophoresis of the present invention (1) may additionally have a heat sink (51, 52) and a cooling fan (61, 62). FIG. 11 is a perspective view illustrating the tissue clearing apparatus using electrophoresis of the present invention (1) according to yet another exemplary embodiment, and FIG. 12 is a section view for the tissue clearing apparatus of the FIG. 11 above.

A pair of heat sinks (51, 52) are connected to the external region of the thermoelements (41, 42), and comprise a number of cooling pins for efficient heat release from the thermoelements (41, 42). A number of cooling pins configured to extrude outward, and thus the heat transferred from the thermoelements is released efficiently.

A pair of cooling fans (61, 62) are placed outside of the heat sinks (51, 52) to face the heat sinks, and consist of a fan operated by an electric motor. The heat on the outside surface of the heat sinks (51, 52) is released outward rapidly by the operation of the cooling fans (61, 62).

The present invention is described by referring to various exemplary embodiments thereof. Although the preferred embodiments of the invention are particularly disclosed herein, one of ordinary skill in the art will readily recognize that the same principles are equally applicable to, and can be implemented in other systems, and that any such variation would be within such modifications that do not part from the scope of the present invention. It is to be understood that the invention is not limited in its application to the details of any arrangement shown, since the invention is capable of other embodiments. The terminology used herein is for the purpose of description and not of limitation. Further, although certain methods are described with reference to certain steps that are presented herein in certain order, in many instances, these steps may be performed in any order as would be appreciated by one skilled in the art, and the methods are not limited to the particular arrangement of steps disclosed herein.

REFERENCE NUMERALS

1: tissue clearing apparatus using electrophoresis
10: chamber
13: inlet port
14: outlet port
15: support member 21, 22: electrodes
31, 32: cooling plate
41, 42: thermoelement
51, 52: heat sink
51a, 52a: cooling pin
61, 62: cooling fan
70: control part

The invention claimed is:

1. A tissue clearing apparatus configured for using electrophoresis for separating components or constituents of a biological tissue, which comprises,
    (a) a chamber able to contain buffer solution and a biological tissue, wherein the chamber has an inlet port and an outlet port therein for circulating the buffer solution;
    (b) a first electrode and a second electrode separately placed in two opposite positions to correspond to each other in the chamber, wherein each electrode is plate-shaped; and
    (c) a cooling plate directly connected to each of the first and second electrode outside of the chamber.

2. The tissue clearing apparatus configured for using electrophoresis of claim 1, wherein each area of the first electrode and the second electrode is not less than 1 cm$^2$, and the distance between the first electrode and the second electrode is not less than 10 mm.

3. The tissue clearing apparatus configured for using electrophoresis of claim 1, wherein a fixed electric current is applied through the first electrode and the second electrode.

4. The tissue clearing apparatus configured for using electrophoresis of claim 3, wherein the fixed electric current is between 0.5 to 3 A (ampere).

5. The tissue clearing apparatus configured for using electrophoresis of claim 1, wherein a control part is provided for switching polarities of the first electrode and the second electrode to each other.

6. The tissue clearing apparatus configured for using electrophoresis of claim 1, wherein a support member for supporting the biological tissue is further comprised in the chamber.

7. The tissue clearing apparatus configured for using electrophoresis of claim 1, wherein each of the first electrode and the second electrode has two or more electrodes, and the first electrode and the second electrode are placed in two opposite positions to correspond to each other, and wherein a control part is provided for controlling any one of two or more first electrodes and any one of two or more second electrodes to operate mutually.

8. The tissue clearing apparatus configured for using electrophoresis of claim 7, wherein the control part controls the first electrode and the second electrode to switch the polarities to each other.

9. The tissue clearing apparatus configured for using electrophoresis of claim 1, wherein the first electrode consists of one electrode and the second electrode consists of two electrodes, and the first electrode and the second electrodes are placed in opposite two positions to correspond to each other, and wherein a control part is provided for controlling the first electrode and any one of the second electrodes to operate mutually.

10. The tissue clearing apparatus configured for using electrophoresis of claim 1, which further comprises the following:
    (a) a thermoelement for cooling down the cooling plate.

11. The tissue clearing apparatus configured for using electrophoresis of claim 10, wherein the cooling plate consists of at least one cooling plate, and is connected to each of the external regions of the first electrode and the second electrode.

12. The tissue clearing apparatus configured for using electrophoresis of claim 11, which further comprises at least one cooling fan, wherein the cooling fan is placed outside of the heat sink, and circulates the surface air on the heat sink.

13. The tissue clearing apparatus configured for using electrophoresis of claim 10, wherein the thermoelement consists of at least one thermoelement connected to the external region of the cooling plate, and wherein the thermoelement further comprises at least one heat sink which is connected to the external region of the thermoelement and has a number of cooling pins.

* * * * *